United States Patent [19]

Toki et al.

[11] Patent Number: 5,081,264
[45] Date of Patent: Jan. 14, 1992

[54] BIOXANTHRACENE DERIVATIVES

[75] Inventors: Shinichiro Toki; Mika Nozawa, both of Tokyo; Mayumi Yoshida, Kanagawa; Hiroshi Sano; Katsuhiko Ando, both of Tokyo; Isao Kawamoto, Kanagawa; Yuzuru Matsuda, Tokyo; Junichi Ikeda; Kazuhiro Kubo, both of Shizuoka, all of Japan

[73] Assignee: Kyowa Hakko Kabushiki Kaisha, Japan

[21] Appl. No.: 584,278

[22] Filed: Sep. 18, 1990

[30] Foreign Application Priority Data

Sep. 28, 1989 [JP] Japan .................................. 1-253098
May 23, 1990 [JP] Japan .................................. 2-133322

[51] Int. Cl.$^5$ ............................................ C07D 311/92
[52] U.S. Cl. ...................................................... 549/389
[58] Field of Search ........................... 549/389; 514/455

[56] References Cited

U.S. PATENT DOCUMENTS 3,892,848 7/1975 Jiu et al. .............................. 549/280

FOREIGN PATENT DOCUMENTS 230370 7/1987 European Pat. Off. .

Primary Examiner—Nicky Chan
Attorney, Agent, or Firm—Schweitzer, Cornman & Gross

[57] ABSTRACT

A compound of formula (I):

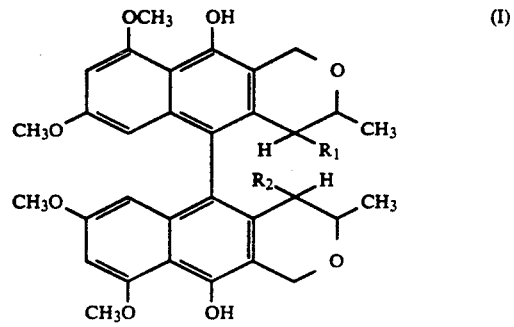

wherein $R_1$ represents hydrogen, hydroxy or acetoxy and $R_2$ represents hydroxy or acetoxy.

The compounds are capable of protecting the nerve cells and also antagonistic activity against N-methyl-D-aspartic acid receptors.

They may be prepared by fermentation of a microorganism of the genus Verticillium or a mutant thereof.

5 Claims, No Drawings

BIOXANTHRACENE DERIVATIVES

The present invention relates to physiologically active compounds which are not only capable of protecting the nervous system but also show antagonistic activity against N-methyl-D-aspartic acid receptors. They thus appear useful for the treatment of nervous disorders and amnesia. More particularly, this invention relates to such compounds elaborated by microorganisms.

Such compounds are useful in the prevention and/or treatment of neurodegeneration in pathological conditions such as stroke, hypoglycaemia, cerebral palsy, transient cerebral ischaemic attack, cerebral ischaemia during cardiac pulmonary surgery and cardiac arrest, perinatal asphyxia, epilepsy, Huntington's chorea, Alzheimer's disease, Olivo-pontocerebellar atrophy, anoxia such as from drowning, spinal cord injury and poisoning by exogenous NMDA poisons (e.g. some forms of lathyrism).

Known compounds of this type are exemplified by MK-801 in EP-A-0230370.

The present invention is based upon the discovery that a microorganism of the genus Verticillum which we have isolated from the soil in Kanagawa-ken, Japan is capable of producing a new range of compounds, which are not only capable of protecting nerve cells but also capable of antagnostic activity against N-methyl-D-aspartic acid receptors.

According to the present invention, there are provided compounds represented by the following general formula (I).

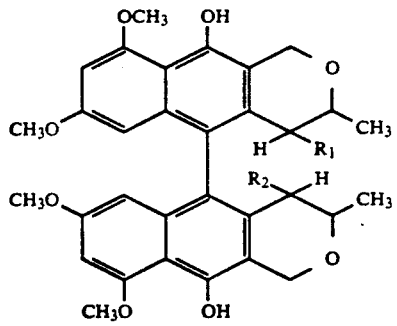

wherein $R_1$ represents hydrogen, hydroxy or acetoxy and $R_2$ represents hydroxy or acetoxy. The compounds are referred to hereinafter as "Compounds ES-242".

Compounds ES-242 are capable of significantly protecting the nervous system and are also antagnostic against N-methyl-D-aspartic acid receptors.

The structure of Compounds ES-242 is related to the structures of Singueanol I and II as shown below, which were isolated from a herbal plant of East African origin and which represent dimers of tetrahydroanthracene. However, it has been reported that Singueanol I and II are neither capable of protecting the nervous system nor antagnostic against N-methyl-D-aspartic acid receptors, even though they exhibit anti-aspartic and anti-bacterial activity.

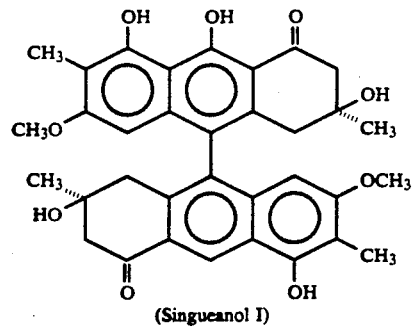
(Singueanol I)

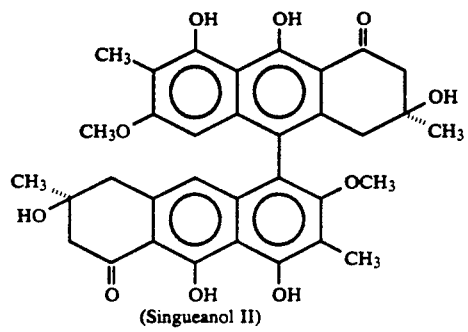
(Singueanol II)

Compounds ES-242 of formula (I) according to the present invention may be classified as follows:

| ES-242   | $R_1$    | $R_2$   |
|----------|----------|---------|
| ES-242-1 | hydrogen | acetoxy |
| ES-242-2 | acetoxy  | acetoxy |
| ES-242-3 | hydroxy  | acetoxy |
| ES-242-4 | hydroxy  | hydroxy |
| ES-242-5 | hydrogen | hydroxy |

PHYSICO-CHEMICAL CHARACTERISTICS OF ES-242

(i) ES-242-1:

①  Nature: light yellowish crystal (neutral substance)
②  Molecular weight: 604
③  Molecular formula: $C_{34}H_{36}O_{10}$
Mass analysis:
Found: SIMS 604 (M+) High resolution EIMS 604.2268
Calculated: 604.2306
④  Melting point: 233° C.–237° C. (decomp.)
⑤  Infrared absorptions spectrum: (KBr method) (cm$^{-1}$) 3380, 1735, 1623, 1576, 1457, 1381, 1361, 1157, 1097, 1060
⑥  Ultraviolet absorption spectrum: (in methanol) $\lambda_{max}$(nm) 347, 309, 297, 239
⑦  $^1$H-NMR spectrum: (500 MHz, CDCl$_3$) 9.49(s, 1H), 9.37(s, 1H), 6.48(d, J=2.2 Hz, 1H), 6.36(d, J=2.2 Hz, 1H), 5.93(d, J=2.2 HZ, 1H), 5.89(d, J=2.2 Hz, 1H), 5.35(d, J=1.6 Hz, 1H), 5.28(d, J=15.7 Hz, 1H), 5.18(d, J=15.4 Hz, 1H), 4.88(d, J=15.4 Hz, 1H), 4.83(d, J=15.7 Hz, 1H), 4.07(s, 3H), 4.03(s, 3H), 3.87(m, 1H), 3.78(d, q, J=6.4, 1.7 Hz, 1H), 3.44(s, 3H), 3.42(s, 3H), 2.15(d, d, J=17.0, 3.1 Hz, 1H), 2.02(d, d, J=17.0, 10.4 Hz, 1H), 1.20(s, 3H), 1.16(d, J=6.2 Hz, 3H), 1.11(d, J=6.4Hz, 3H),
⑧  $^{13}$C-NMR spectrum: (125 MHz, CDCl$_3$) 169.0(s), 157.5(s), 157.3(s), 157.2(s), 156.6(s), 149.3(s), 149.1(s), 135.4(s), 135.1(s), 133.7(s), 130.9(s), 126.9(s), 122.6(s), 115.4(s), 115.2(s), 110.6(s), 109.3(s), 98.5(d), 98.4(d), 97.8(d), 96.7(d), 73.5(d) 70.2(d), 66.8(d), 65.2(t), 64.6(t), 59.3(q), 56.2(q), 55.2(q), 55.1(q), 34.5(t), 21.5(q), 19.4(q), 17.0(q)

⑨ Specific rotation: $[\alpha]_D^{27} = +11°$ (c=0.46, methanol)

⑩ Solubility: Readily soluble in methanol, acetone, ethyl acetate and chloroform. Insoluble in water and n-hexane.

(ii) ES-242-2

① Nature: light yellowish powder (neutral substance)
② Molecular weight: 662
③ Molecular formula: $C_{36}H_{38}O_{12}$
Mass analysis:
Found: SIMS 662 (M+) High resolution EIMS 662.2357
Calculated: 662.689
④ Melting point: 161° C.-162° C.
⑤ Infrared absorptions spectrum: (KBr method) (cm$^{-1}$) 3400, 1735, 1620, 1580, 1460, 1380, 1360, 1230, 1150, 1090, 1045
⑥ Ultraviolet absorption spectrum: (in methanol) $\lambda_{max}$(nm) 354, 338, 309, 297, 239
⑦ $^1$H-NMR spectrum: (400 MHz, CDCl$_3$) 9.46(s, 1H), 6.42(d, J=2.2 Hz, 1H), 5.90(d, J=2.2 Hz, 1H), 5.42(d, J=1.7 HZ, 1H), 5.27(d, J=15.6 Hz, 1H), 4.88(d, J=15.6 Hz, 1H), 4.05(s, 3H), 3.96(d, q, J=6.4, 1.7 Hz, 1H), 3.40(s, 3H), 1.13(s, 3H), 1.12(d, J=6.4 Hz, 3H)
⑧ $^{13}$C-NMR spectrum: (100 MHz, CDCl$_3$) 169.0(s), 157.2(s), 156.9(s), 149.7(s), 135.6(s), 131.2(s), 125.1(s), 115.8(s), 110.5(s), 98.9(d), 97.9(d), 73.3(d) 66.9(d), 65.1(t), 56.3(q), 55.2(q), 19.2(q), 16.9(q)
⑨ Specific rotation: $[\alpha]_D^{21} = +44°$ (c=0.15, CHCl$_3$)
⑩ Color reaction:
Positive in the reactions with FeCl$_3$, I$_2$, H$_2$SO$_4$ and Ce(SO$_4$)$_2$—H$_2$SO$_4$.

(iii) ES-242-3

① Nature: light yellowish powder (neutral substance)
② Molecular weight: 620
③ Molecular formula: $C_{34}H_{36}O_{11}$
Mass analysis:
Found: SIMS 620 (M+) High resolution EIMS 620.2246
Calculated: 620.6518
④ Melting point: 137° C.-139° C.
⑤ Infrared absorptions spectrum: (KBr method) (cm$^{-1}$) 3400, 1735, 1625, 1575, 1455, 1380, 1355, 1220, 1145, 1085, 1040
⑥ Ultraviolet absorption spectrum: (in methanol) $\lambda_{max}$(nm) 355, 309, 239
⑦ $^1$H-NMR spectrum: (400 MHz, CDCl$_3$) 9.54(s, 1H), 9.45(s, 1H), 6.46(d, J=2.2 Hz, 1H), 6.41(d, J=2.2 Hz, 1H), 5.96(d, J=2.2 HZ, 1H), 5.92(d, J=2.2 Hz, 1H), 5.34(d, J=1.7 Hz, 1H), 5.29(d, J=15.7 Hz, 1H), 5.23(d, J=15.6 Hz, 1H), 4.89(d, J=15.6 Hz, 1H), 4.81(d, J=15.7 Hz, 1H), 4.06(s, 3H), 4.04(s, 3H), 3.87(Bd, Ca, J=6.4 Hz, 1H), 3.85(d, q, J=6.4, 1.3 Hz, 1H), 3.78(d, q, J=6.4, 1.7 Hz, 1H), 3.43(s, 3H), 3.42(s, 3H), 1.42(d, J=6.6 Hz, 1H), 1.28(d, J=6.4Hz, 3H), 1.13(s, 3H), 1.10(d, J=6.4 Hz, 3H)
⑧ $^{13}$C-NMR spectrum: (100 MHz, CDCl$_3$) 168.9(s), 157.9(s), 157.4(s), 157.3(s), 157.0(s), 149.94(s), 149.85(s), 136.1(s), 135.7(s), 135.6(s), 131.3(s), 125.3(s), 123.8(s), 115.5(s), 114.7(s), 110.6(s), 110.4(s), 99.0(d), 98.6(d), 98.1(d), 97.7(d), 73.9(d) 73.7(d), 66.8(d), 66.7(d), 65.2(t)X2, 56.4(q), 56.3(q), 55.3(q), 55.2(q), 19.2(q), 17.1(q), 17.0(q)

⑨ Specific rotation: $[\alpha]_{546}^{22} = +50°$ (c=0.16, CHCl$_3$)
⑩ Color reaction:
Positive in the reactions with FeCl$_3$, I$_2$, H$_2$SO$_4$ and Ce(SO$_4$)$_2$—H$_2$SO$_4$.

(iv) ES-242-4

① Nature: Colorless crystal (neutral substance)
② Molecular weight: 578
③ Molecular formula: $C_{32}H_{34}O_{10}$
Mass analysis:
Found: SIMS 578 (M+) High resolution EIMS 578.2104
Calculated: 578.6146
④ Melting point: 184° C.-185° C.
⑤ Infrared absorptions spectrum: (KBr method) (cm$^{-1}$) 3400, 1620, 1575, 1455, 1375, 1355, 1250, 1195, 1150, 1085, 1040
⑥ Ultraviolet absorption spectrum: (in methanol) $\lambda_{max}$(nm) 351, 336, 309, 297, 238
⑦ $^1$H-NMR spectrum: (400 MHz, CDCl$_3$) 9.53(s, 1H), 6.45(d, J=2.2 Hz, 1H), 5.99 (d, J=2.2 Hz, 1H), 5.24(d, J=15.8 HZ, 1H), 4.81 (d, J=15.8 Hz, 1H), 4.05(s, 3H), 3.81(Bs, 1H), 3.67(d, q, J=6.4, 1.4 Hz, 1H), 3.45(s, 3H), 1.46(Bs, 1H), 1.27(d, J=6.4 Hz, 3H),
⑧ $^{13}$C-NMR spectrum: (100 MHz, CDCl$_3$) 157.9(s), 157.6(s), 150.1(s), 136.1(s), 135.7(s), 123.9(s), 114.4(s), 110.5(s), 98.4(d), 98.0(d) 73.9(d), 66.7(d), 65.3(t), 56.4(q), 55.3(q), 17.1(q),
⑨ Specific rotation: $[\alpha]_D^{21} = +54°$ (c=0.18, in CHCl$_3$)
⑩ Color reaction:
Positive in the reactions with FeCl$_3$, I$_2$, H$_2$SO$_4$ and Ce(SO$_4$)$_2$—H$_2$SO$_4$.

(v) ES-242-5

① Nature: light yellowish powder (neutral substance)
② Molecular weight: 562
③ Molecular formula: $C_{32}H_{34}O_9$
Mass analysis:
Found: SIMS 562 (M+) High resolution EIMS 562.221
Calculated: 562.220
④ Melting point: 157° C.-158° C.
⑤ Infrared absorptions spectrum: (KBr method) (cm$^{-1}$) 3400, 1625, 1575, 1455, 1375, 1355, 1245, 1190, 1140, 1080, 1035
⑥ Ultraviolet absorption spectrum: (in methanol) $\lambda_{max}$(nm) 346, 337, 308, 298, 282, 238
⑦ $^1$H-NMR spectrum: (400 MHz, CDCl$_3$) 9.48(s, 1H), 9.45(s, 1H), 6.47(d, J=2.2 Hz, 1H), 6.40(d, J=2.2 Hz, 1H), 5.97(d, J=2.2 HZ, 1H), 5.96(d, J=2.2 Hz, 1H), 5.25(d, J=15.8 Hz, 1H), 5.19(d, J=15.5 Hz, 1H), 4.84(d, J=15.8 Hz, 1H), 4.82(d, J=15.5 Hz, 1H), 4.06(s, 3H), 4.04(s, 3H), 3.81(d, d, J=4.7, 1.2 Hz, 1H), 3.74(m, 1H), 3.67(d, 1, J=6.2 Hz, about 1.2 Hz, 1H), 3.46 (s, 3H), 3.45(s, 3H), 2.13~1.98(m, 2H), 1.56(d, J=4.7 Hz, 1H), 1.27(d, J=6.4 Hz, 3H), 1.16(d, J=6.2 Hz, 3H)
⑧ $^{13}$C-NMR spectrum: (100 MHz, CDCl$_3$) 157.8(s), 157.6(s)X2, 157.3(s), 149.5(s), 149.4(s), 135.8(s), 135.3(s), 135.2(s), 134.1(s), 125.4(s), 122.7(s), 115.3(s), 114.3(s), 110.5(s), 109.3(s), 98.2(d), 97.7(d), 97.5(d), 97.3(d), 73.9(d), 70.4(d) 66.6(d), 65.3(t), 64.5(t), 56.3(q), 56.2(q), 55.30(q), 55.27(q), 34.4(t), 21.5(q), 17.1(q)

⑨ Specific rotation: $[\alpha]_D^{20} = +21°$ (c=0.12, CHCl$_3$)

⑩ Color reaction:

Positive in the reactions with FeCl$_3$, I$_2$, H$_2$SO$_4$ and Ce(SO$_4$)$_2$—H$_2$SO$_4$.

The following instruments were used to measure the above-mentioned data:

Melting point: Micro melting point measuring device (commercial product of Yanagimoto Seisakusho, Japan).

Infrared absorptions spectrum: IR-27G IR spectrophotometer (commercial product of Shimadzu Seisakusho, Japan)

Ultraviolet absorption spectrum: 200-20 Type Double beam spectrophotometer (commercial product of Hitachi Seisakusho, Japan).

NMR Spectrum: AM-500 NMR device for ES-242-1 and AM-400 NMR device for ES-242-2 - ES-242-5 (commercial products of Bruker).

Specific rotation:

DIP-370 Digital polarimeter (commercial products of Nihon Bunko, K. K., Japan)

Mass spectrum: M-80B Mass spectrometer (commercial products of Hitachi Seisakusho, Japan).

The above-mentioned data have revealed that all the compounds of the present invention are novel.

Rf values of compounds ES-242 were measured by thin layer chromatography using various developers in the following Test Nos. 1–4.

Test No. 1

Thin Layer: Kieselgel 60F$_{254}$(Merck, Art 5628).
Developer: n-hexane/acetone (1:1).
Developing method: Room temperature, ascending method, 15–60 minutes.

Test No. 2

Developer: chloroform/ethyl acetate (1:1). Other conditions are the same as Test No. 1.

Test No. 3

Developer: n/hexane/acetone (3:2). Other conditions are the same as Test No. 1.

Test No. 4

Thin layer: RP-18 (Merck, Art 13724).
Developer: 100% methanol.
Other conditions are the same as Test No. 1.

The compounds were detected by the iodine reaction or by irradiation of ultraviolet rays at 253.7 nm. The results are shown in the following Table 1

TABLE 1

| Compound | Rf value | | | |
|---|---|---|---|---|
| | Test No. 1 | 2 | 3 | 4 |
| ES-242-1 | 0.72 | 0.53 | * | * |
| ES-242-2 | * | * | 0.30 | 0.76 |
| ES-242-3 | * | * | 0.26 | 0.78 |
| ES-242-4 | * | * | 0.24 | 0.80 |
| ES-242-5 | * | * | 0.32 | 0.72 |

Note: *not measured.

Preparation of Compounds ES-242

Compounds ES-242 may be obtained culturing a microorganism of the genus Verticillium capable of producing compounds ES-242 in a medium to accumulate compounds ES-242 in the cultured broth and recovering compounds ES-242 from the cultured broth.

Any and all microorganisms belonging to the genus Verticillium and capable of producing compounds ES-242 may be used for the purpose of the present invention. Also, any and all mutant strain thereof may be used. Examples of such mutant strains include those induced artificially, for example, by irradiation of ultraviolet rays or X-rays and those induced by using mutagents and naturally-occurring mutant strains so far as they are capable of producing compounds ES-242.

In one preferred embodiment of the present invention, a strain named by us as Verticillium sp. SPC-15898 having the following mycological characteristics, is used.

① Observation with unaided eyes 10 days after an initial culturing of this strain at a temperature of 20° C. on malt extract agar medium, the diameter of the colonies produced reached 13–16 mm. Each colony had a white and downy surface and its back was colored light orange.

10 days after an initial culturing at a temperature of 20° C. on potato-glucose agar medium, the diameter of the colonies produced reached 16–19 mm. Each colony had a white and downy surface and its back was a dark, dull brown color.

The growth temperature of this strain is optimally 10° C.–33° C. and preferably 20° C.–28° C. The growth pH is 2–11 and preferably 6–8.

② Microscopic observation when cultured on malt extract agar medium

Each hyphae has partition, is colorless and well branched, and rarely forms bundles. Phialides exist singly, or from whorls in the aerial mycelia. In some cases, conidophore grows upwardly from aerial mycelium and is branched 1–3 times. 3–5 phialides are found at the top end of conidophore.

The phialide is colorless, smooth and in the form of a drill or inverted rod. It has a length of 8–23 $\mu$m and a width of not greater than 1.5–2 $\mu$m. The phialide is tapered to measure a width of 0.3–0.5 $\mu$m at the end. Ontogenensis of conidium is the endogensis budding type. Conidia form a solid mass at the end of the phialide. The longitudinal axis of the conidium extends obliquely or vertically with respect to the longitudinal axis of the phialide.

The philo-type conidiumis monocellular, colorless and smooth and is in the form of an oblique, long oblique, inverted egg or oblique having slightly depressed surfaces on both sides shape. The conidium has a length of 3.5–5 $\mu$m and a width of 1–2 $\mu$m. Chlamydospore is not formed. With regard to this strain, the anamorph as set forth is observed, bu the telemorph is not found.

With reference to the above-mentioned mycological characteristics and to Cephalosporium-artige Schimmelpilze (Hyphomycetes) written by Walter Gams and published by Gustav Fischer Verlag, Stutgart (1971), the classification of this strain was studied and it was concluded that the present microorganism is classified into the genus Verticillium.

This strain was designated by us as Verticillium sp. SPC-15898 and was filed with the Research Institute of Microbiological Industry, Agency of the Industrial Technology, the Japanese Government (Bikoken) on 20th September 1989 under the Budapest Treaty. The deposition number of this strain is FERM-BP 2604.

The present microorganism may be cultured in a conventional manner applicable to the culturing of various molds. Both synthetic and organic media may be used for the purpose of the present invention so far as they contain suitable amounts of assimilable sources of carbon, nitrogen, inorganic substances and the like.

Carbon sources which may be used for the purpose of the present invention are exemplified by various carbohydrates such as glucose, fructose, sucrose, stabilose, starch, dextrin, mannose, maltose and molasses; organic acids such as citric acid, malic acid, acetic acid and fumaric acid; alcohols such as methanol and ethanol; hydrocarbons such as methane, ethane, propane and n-paraffin: amino acids such as glutamic acid; and glycerol.

Examples of suitable nitrogen sources include ammonium salts such as ammonium chloride, ammonium sulfate, ammonium nitrate and ammonium phosphate; amino acids such as aspartic acid, glutamine, cystine and alanine; urea, peptone, meat extract, yeast extact, dried yeast, corn steep liquor, soyabean powder, cotton seed cake, soyabean casein, cazamino acid and Pharmamedia.

Suitable inorganic substances are exemplified by potassium monohydrogen phosphate, potassium dihydrogen phosphate, sodium dihydrogen phosphate, magnesium sulfate, ferrous sulfate, magnesium sulfate, copper sulfate, cobalt sulfate, zinc sulfate, calcium pantothenate, ammonium molybdate, aluminum potassium sulfate, barium carbonate, calcium carbonate, cobalt chloride and sodium chloride.

If desired or necessary, it is possible to add to the medium substances such as vitamins, which are capable of promoting the growth of the microorganism or enhancing the productivity of compounds ES-242. Where the microorganism used requires a special substance for the growth, it is possible to add such a substance to the medium.

Culturing may be effected, for example, with shaking or aeration and shaking at a temperature of 20° C.–40° C. and at a neutral pH. After being cultured for 3–15 m days, the amount of compounds ES-242 accumulated in the medium reaches the maximum.

Compounds ES-242 may be recovered from the medium and isolated in a conventional manner, e.g. as used for the recovery of various physiologically active substances from cultured broth.

For example, compounds ES-242 may be recovered and isolated by the extraction of active components from the cells using organic solvents such as acetone and methanol, removal of the cells by filtration and centrifugation, column chromatography or thin layer chromatography using absorbing resins, silica gel, silanized silica gel, reversed silica gel, aluminum, cellulose, diatom earth, magnesium silicate, gel filtration agents or ion exchange resins and the like, followed by separation using suitable solvents.

In a preferred embodiment of the present invention, compounds ES-242 may be isolated from their cultured broth in the following manner.

The cultured broth is filtered or centrifuged to separate the cells, which are then extracted by using an organic solvent. Alternatively, the supernatant of the cultured broth is adsorbed by using a suitable resin and is then eluted by using a suitable solvent. The resultant extracted solution or eluate may be concentrated under reduced pressure to remove the solvent. The resultant aqueous solution is then extracted by adding a solvent which is not miscible with water (such as, ethyl acetate, butyl acetate or hexane). The extracted solution is concentrated under reduced pressure and subjected to silica gel chromatography to adsorb the active substances, followed by the use of an appropriate solvent such as chloroform.

The eluate is subjected to, for example, silica gel chromatography, reversed silica gel chromatography or high performance liquid chromatography to adsorb the active substances. Elution is further effected by using a suitable solvent to obtain the ES-242.

In the above-mentioned purifying step, ES-242 may be detected by thin layer chromatography using fluorescence-dyed silica gel (Kieselgel $F_{254}$, Merck), followed by the iodine reaction or irradiation of ultraviolet rays at 253.7 nm.

The following non-limiting Examples illustrate the present invention.

EXAMPLE 1

Verticillium sp. SPC-15898 (FERM-BP 2604) was used as a seed strain. The seed strain (one platinum loop) was cultured with shaking at a temperature of 25° C. for 5 days using a first medium (10 ml; pH 6.4) large test tube (capacity 50 ml), the composition of the first medium being V8 vegetable juice (20 ml/dl; commercial product of Cambel, U.S.A.) and calcium carbonate (0.3 g/dl).

The resultant first cultured broth (5 ml) was transferred to a second medium (50 ml) in an Erlenmeyer flask (capacity 300 ml) having the same composition as that of the first medium, and for culturing at a temperature of 25° C. for 2 days. The resultant second cultured broth (50 ml) was further cultured by using a medium (500 ml) in an Erlenmeyer flask (capacity 2 l) equipped with a baffle. The main culturing was effected at a temperature of 25° C. for 5 days with shaking. The composition of the main medium was glucose (2.0 g/dl), Mush potato no moto (2.0 g/dl; condensed mushed potato, commercial product of Yuki Jirushi Nyugyo K. K., Japan), potassium dihydrogen phosphate (0.05 g/dl) and magnesium phosphate (0.05 g/dl) [pH 6.0].

The cells were separated from the resultant cultured broth (5 l) by centrifugation (7000 r.p.m.) and methanol (4 l) was added to the separated cells. The material was allowed to stand at a temperature of 4° C. for 24 hours while stirring. Then the cells were removed by filtration.

The resultant methanol extract (about 4 l) was reduced to about 150 ml by concentration under reduced pressure and was extracted 5 times with hexane (each 500 ml). By drying the hexane layer under reduced pressure, a brown oily substance (about 2.0 g) was obtained. The oily substance was dissolved in 5 ml of chloroform and put onto the top portion of a column (200 ml) which had been packed with silica gel (Wako gel; commercial product of Wako Junyaku K. K., Japan) and which had been filled with chloroform. Elution of the active substance was effected using chloroform. The eluate was divided into fractions (each 10 g) which were numbered in regular order. Each fraction was detected by thin layer chromatography. Fraction Nos. 58–74 contained ES-242-1. The active fractions were collected and combined. The combined fractions were dried under reduced pressure to obtain light yellowish powders (about 250 mg). The powders were washed with a mixture (1 ml) of hexane/acetone (9:1) and then excess of the solvent was removed by evaporation under reduced pressure to obtain crude powders (about 26 mg), which were dissolved n methanol (1 ml), followed by allowing them to stand at a temperature of 5° C. for one day. There ware obtained light yellowish crystals (about 15 mg).

EXAMPLE 2

Verticillium sp. SPC-15898 (FERM-BP 2604) was used as a seed strain. The composition of the first medium used (pH 6.4) was V8 vegetable juice (20 ml/dl; commercial product of Cambel) and calcium carbonate (0.3 g/dl). The seed strain (one platinum loop) was transferred to the first medium (40 ml) in an Erlenmeyer flask (capacity 250 ml) for culturing with shaking at a temperature of 25° C. for 4 days.

The resultant first cultured broth (30 ml) was divided into 6 fractions, which were respectively cultured by using 6 media ( each 300 ml), each having the same compositions as the composition of the first medium and each in an Erlenmeyer flask (capacity 2 l) equipped with a baffle. The second culturing was effected at a temperature of 25° C. for 2 days.

The resultant second cultured broth (1.8 l) in total) was transferred to a third medium (100 l) put in a culturing vessel (capacity 200 l). The third medium has the same composition as the composition of the first medium. The third culturing was effected at a temperature of 25° C. for 2 days.

The resultant third cultured broth (100 l) was transferred to a main culture medium (1 kl) in a culturing vessel (capacity 2 kl). The main medium (pH 6.0) had the following composition glucose (2.0 g/dl), petone (2.0 g/dl), potato starch (2.0 g/dl), potassium dihydrogen phosphate (0.5 g/dl) and magnesium phosphate (05 g/dl)

the main culturing was effected at a temperature of 25° C. for 4 with shaking.

After completion of the culturing, diatom earth (80 kg) was added to the cultured broth (1000 l) which was then filtered to collect the cells. After addition of n-propanol (600 l) with stirring, the cells were removed by filtration. The filtrate was diluted with water (1200 l) and the diluted solution was passed through a column (60 l) which had been packed with Diaion HP-20 (commercial product of Mitsubishi Kasei Kogyo K. K., Japan) and which had been washed with 60% methanol (200 l). Elution was effected by using acetone (250 l). The eluate was concentrated under reduced pressure, and extracted with hexane (20 l). The water layer was further extracted by the addition of ethyl acetate (10 l).

The hexane layer was dried under reduced pressure to obtain an oil substance colored brown, which was then dissolved in chloroform (300 ml). The solution was put onto the top portion of a column (2l) which had been packed with silica gel (Wako gel, commercial product of Wako Junyaku, K. K., Japan), and which had been filled with chloroform.

After washing the column with chloroform, elution was effected by using a mixed solution of chloroform and methanol (99:1). The eluates were collected, combined and dried under reduced pressure. The dried material was dissolved in 70% methanol and put onto the top portion of a column (600 ml) which had been packed with YMC-ODS (commercial product of Yamamura Kakgaku K. K., Japan) and which had been come to equilibrium with the same solvent.

Elution was effected with 70% methanol, and the absorbance was detected by using a spectrophotometer (UVDEC-100-III, commercial product of Nihon Bunko K. K., Japan). ES-242-2 (133 mg) was recovered with reference to a large peak observed at 242 nm.

The ethyl acetate layer was concentrated under reduced pressure. A portion (37.1 g) thereof was dissolved in a small amount of chloroform and was put on the top portion of a column (2 l) which had been packed with silica gel (Art. 7734, commercial product of Merck) and which had been equilibrated by using chloroform. Elution was effected by using chloroform. The eluate was collected and dried under reduced pressure to give an oily substance (7 g), which was then dissolved in a small amount of chloroform. A small amount of diatom earth was added to the solution. The mixture was dried under reduced pressure. The dried substance was put onto a top portion of a column (500 ml) which had been packed with silica gel (Wako gel, commercial product of Wako Junyaku K. K., Japan) and which had been filled with a mixed solvent of hexane/acetone (9:1).

Elution was effected by using a mixture of hexane/acetone (8:2). The eluate was divided into fractions (each 17 ml). Fraction Nos. 135–176 contained ES-242-5. The active fractions were collected, combined and subjected to silica gel chromatography, in a similar manner to that described above, to obtain ES-242-5 (77 mg).

The silica gel column which had been eluted three times with a mixed solution of hexane/acetone (8:2) was then eluted with ethyl acetate to give fractions containing ES-242-3 and ES-242-4. These fractions were dried under reduced pressure.

The dried material was dissolved by adding a small amount of chloroform. Then a small amount of diatom earth was added thereto and the mixture was dried under reduced pressure. The dried material was put onto the top portion of a column (300 ml) which had been packed with silica gel (Art. 9385, commercial product of Merck) and which had been filled with a mixed solution of hexane/acetone (7:3). Elution was effected using a mixed solution of hexane/acetone (7:3).

The eluate was divided into fractions (each 17 ml). Fraction Nos. 51–67 contained ES-242-3 and Nos. 78–96 contained ES-242-4.

Fraction Nos. 78–96 were collected, combined and dried under reduced pressure. The dried material was dissolved in acetone. By adding hexane in drops to the solution, crystals of ES-242-4 (102 mg) were obtained.

Fraction Nos. 51–67 were collected, combined and dried under reduced pressure. Th dried material was put onto the top portion of a silica gel column (150 ml) which had been packed with Art. 9385 and which had been filled with a mixed solution of hexane/acetone (7:3). Elution was effected using a mixed solution of hexane/ acetone (7:3). The eluate was divided into fractions (each 15 ml). Fraction Nos. 45–56 contained ES-242-3. The active fractions were collected, combined and dried. The dried material was dissolved in 70% methanol and put onto the top portion of a reversed silica gel column (20 ml) which had been packed with YMC-ODS; commercial product of Yamamura Kagaku K. K., Japan). Elution was effected by using 70% methanol. By the use of a spectrophotometer (UVDEC-100-III; commercial product of Nihon Bunko K. K., Japan), the absorbance of the eluate was detected. With reference to a large peak appearing at 242 nm, there was obtained ES-242-3 (2.6 mg).

According to a further feature of the present invention, the compounds of formula (I) as herein defined may be used in the protection of the nervous system and for antagonistic activity against N-methyl-D-asparitic acid receptors.

The following Experiments illustrate the activity of the compounds of the present invention.

EXPERIMENT 1

Protection of cultured nerve cells

The septal area was taken out from the brain of a fetal rat. The cells were dispersed using trypsin and deoxyribonuclease and were cultured for one day on a Pit medium (Dulbecco modified Eagle medium or Ham F12 medium, commercial products of Nissui Seiyaku K. K., Japan) containing 5% horse serum and 5% fetal calf serum. After adding cytosine arabinoide (10μM) to the medium, the culturing was continued for 10 days.

L-glutamic acid (100 μM) and ES-242-1 were added to the cultured broth to measure the survival ratio of the nerve cells. For control purposes, a similar procedure was carried out with the exception that glutamic acid (100μM) and/or ES-242-1 were replaced by dimethylsulfoxide (DMSO) (0.5%). The cells which survived were counted by the fluorescence-dying method with reference to the Costa et al. method [Proc. Natl. Acad. Sci., U.S.A., 85, 7351–7355 (1988)].

The results are shown in the following Table 2. The results shown in the following Table 3 were obtained in a manner similar to that described above except the cerebellum was used instead of the septal area. In the following tables, the term "GA" denotes L-glutamic acid (unit 100μM) and the term "SR" denote the survival ratio of the cells (%).

TABLE 2

| Sample | SR (%) |
| --- | --- |
| Control | 87 |
| GA | 5 |
| GA + ES-242-1 (0.1 μg/ml) | 23 |
| GA + ES-242-1 (0.5 μg/ml) | 73 |
| GA + ES-242-2 (5 μg/ml) | 74 |
| GA + ES-242-2 (50 μg/ml) | 74 |

TABLE 3

| Sample | SR (%) |
| --- | --- |
| Control | 90 |
| GA | 44 |
| GA + ES-242-1 (5 μg/ml) | 75 |

Tables 2 and 3 indicate that ES-242-1 inhibited the death of the nerve cells, induced by L-glutamic acid and that its activity depends upon the dose of the compound used. ES-242 is also shown to be significantly effective.

EXPERIMENT 2

Protection of cultured nerve cells

The results shown in the following Tables 4 and 5 were obtained by a procedure similar to that described in Experiment 1 above with the exception that the cerebellum of a rat and ES-242-2 or ES-242-5 were respectively used instead of the septal area and ES-242-1.

TABLE 4

| Sample | SR (%) |
| --- | --- |
| Control | 95 |
| GA | 56 |
| GA + ES-242-2 (1 μg/ml) | 44 |
| GA + ES-242-2 (10 μg/ml) | 88 |

TABLE 5

| Sample | SR (%) |
| --- | --- |
| Control | 88 |
| GA | 40 |
| GA + ES-242-5 (1 μg/ml) | 68 |
| GA + ES-242-5 (5 μg/ml) | 73 |
| GA + ES-242-5 (10 μg/ml) | 79 |

Tables 4 and 5 indicate that compounds ES-242-2 and ES-242-5 also inhibit the death of the nerve cells induced by L-glutamic acid and that the inhibiting activity again depends upon the dose of the compound used.

EXPERIMENT 3

Protection of nerve cells from ischaemic injury

Ischaemic injury of the nervous system was induced in the CAI area of the hippocampus of Mongolian gerbils by closing and reperfusing two cartoid arteries with reference to the Kirino et al method [Cerebral Nerve, Vol. 38, No. 12, 1157–1163 (1986)] as follows.

On each occasion, the test compound was suspended in a physiological solution of sodium chloride. The animal (body weight 60–70 g) was anesthetized with ether. The left and right common cartoid arteries were exposed through midcervical vertical skin incision and the anesthetic was discontinued. The cartoid arteries on both sides were occluded for 5 minutes using aneurism clips. Immediately after this, a given amount (100 mg/kg) of Compound ES-242-1 was given orally to the animal. One week after this, the animal was fixed by transcardic perfusion. Immediately after this, the brain was removed from the animal to prepare a sample of the histologic section containing the CIA area of the hippocampus. The number of normal cells of the CAI area neurons per 1 mm linear length was counted.

The above-mentioned treatment is hereinafter referred to as the ischaemic treatment.

For control purposes, a group of the animals were given a physiological solution of sodium chloride only, without ischaemic treatment. There was also an ischaemic group wherein each animal was subjected to the ischaemic treatment, followed by administration of a physiological solution of sodium chloride without the test compound. The results are shown in Table 6, from which it is apparent that ES-242-1 exhibited a significant protecting activity to ischaemic injury of the nervous system at a dose of 100 mg/kg.

TABLE 6

| Group | A | D | I | N |
| --- | --- | --- | --- | --- |
| 1 | 3 | 0 | — | 100 ± 4.7 |
| 2 | 5 | 0 | + | 0 ± 0 |
| 3 | 5 | 100 | + | 24.4 ± 20.6 |

Notes:-
Group 1 . . . control (normal); Group 2 . . . control (ischaemic); Group 3 . . . administered with ES-242-1; A . . . number of the animals; D . . . dose (mg/kg); I . . . ischaemic treatment; N . . . number of normal cells/mm in average ± standard deviation

EXPERIMENT 4

The binding activity of Compounds ES-242 to N-methyl-D-aspartic acid receptor was measured as follows.

With reference to the modified method of Vignon et al [Brain Research, 280, 194–197 (1983)], the binding activity of ES-242 to N-[1-(2-thienyl) cyclohexyl]-3,4-[$^3$H]piperidine ([$^3$H]TCP) in rat brain membranes was measured by the use of a crushed cerebrum of a rat and expressed by IC$_{50}$ viz. a concentration required for 50% inhibition of the binding ability to the sample. The results are shown in Table 7.

TABLE 7

| Compound | IC$_{50}$ (μg/ml) |
|---|---|
| ES-242-1 | 0.1 |
| ES-242-2 | 1.9 |
| ES-242-3 | 1.8 |
| ES-242-4 | 14.6 |
| ES-242-5 | 0.6 |

According to a further feature of the present invention, there is provided a pharmaceutical composition comprising a compound of formula (I) as herein before defined in admixture with a pharmaceutically acceptable carrier, diluent or excipient.

The present invention also extends to the use of a compound of formula (I) as hereinbefore defined for the manufacture of a medicament for protecting the nervous system and for antagnostic activity against N-methyl-D-aspartic acid receptors.

We claim:

1. A compound of formula I:

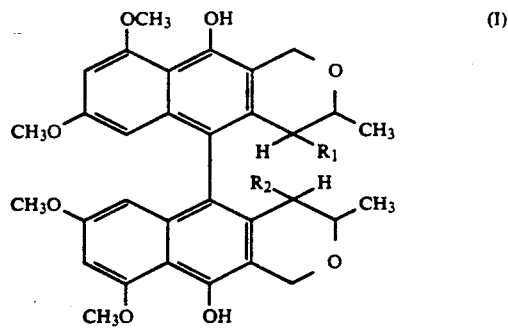

wherein R$_1$ represents hydrogen or hydroxy and R$_2$ represents hydroxy or acetoxy or R$_1$ and R$_2$ represent acetoxy.

2. A compound according to claim 1 wherein R$_1$ is hydrogen and R$_2$ is acetoxy.

3. A compound according to claim 1 wherein R$_1$ is hydroxy and R$_2$ is acetoxy.

4. A compound according to claim 1 wherein R$_1$ and R$_2$ are hydroxy.

5. A compound according to claim 1 wherein R$_1$ is hydrogen and R$_2$ is hydroxy.

* * * * *

UNITED STATES PATENT AND TRADEMARK OFFICE
CERTIFICATE OF CORRECTION

PATENT NO. : 5,081,264
DATED : January 14, 1992
INVENTOR(S) : TOKI, et al.

It is certified that error appears in the above-identified patent and that said Letters Patent is hereby corrected as shown below:

On the title page item [73] Assignee; should read

--KYOWA HAKKO KOGYO KABUSHIKI KAISHA--.

Signed and Sealed this

Sixteenth Day of February, 1993

Attest:

STEPHEN G. KUNIN

*Attesting Officer*   Acting Commissioner of Patents and Trademarks